(12) United States Patent
Dressler et al.

(10) Patent No.: US 8,070,734 B2
(45) Date of Patent: Dec. 6, 2011

(54) ARRANGEMENT FOR THE REMOVAL OF WASTE PRODUCTS DURING THE ABLATION OF BIOLOGICAL TISSUE

(75) Inventors: Georg Dressler, Gera (DE); Axel Möbius, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 39 days.

(21) Appl. No.: 11/587,743

(22) PCT Filed: Apr. 26, 2005

(86) PCT No.: PCT/EP2005/004434
§ 371 (c)(1),
(2), (4) Date: Jul. 24, 2007

(87) PCT Pub. No.: WO2005/105173
PCT Pub. Date: Nov. 10, 2005

(65) Prior Publication Data
US 2008/0103488 A1    May 1, 2008

(30) Foreign Application Priority Data
Apr. 30, 2004 (DE) .......................... 10 2004 021 680

(51) Int. Cl.
*A61M 1/00* (2006.01)
*A61B 17/00* (2006.01)
*A61B 18/18* (2006.01)
(52) U.S. Cl. ................. 604/313; 604/317; 606/1; 606/4
(58) Field of Classification Search .................. 604/540, 604/313, 317; 606/166, 4; 219/121.84
See application file for complete search history.

(56) References Cited

U.S. PATENT DOCUMENTS

| 5,156,618 | A | | 10/1992 | Fiore et al. |
| 5,181,916 | A | | 1/1993 | Reynolds et al. |
| 5,344,418 | A | | 9/1994 | Ghaffari |
| 5,496,985 | A | * | 3/1996 | Foltz et al. ............... 219/121.67 |
| 5,630,807 | A | * | 5/1997 | Joffe ............................. 604/315 |
| 5,971,977 | A | * | 10/1999 | Korenfeld ........................ 606/1 |

(Continued)

FOREIGN PATENT DOCUMENTS

| DE | 197 27 573 C1 | 5/1998 |
| DE | 100 20 522 A1 | 12/2000 |
| DE | 101 29 650 A1 | 1/2003 |
| DE | 101 38 867 A1 | 3/2003 |
| EP | 0 412 789 B1 | 1/1996 |
| WO | WO 93/16741 | 9/1993 |
| WO | WO 99/66843 | 12/1999 |

OTHER PUBLICATIONS

Ernest Beckmann et al., "Digitaltechnik," *Ein Einführungskurs Für das Selbststudium und den Medienverbund*, VDI-Verlag GmbH, pp. 96-101 (1976)/ ("Digital Technology", *An Introduction Course for the Self-Study and the Media Association*).

*Primary Examiner* — Leslie Deak
*Assistant Examiner* — Susan Su
(74) *Attorney, Agent, or Firm* — Patterson Thuente Christensen Pedersen, P.A.

(57) ABSTRACT

The invention relates to an arrangement for the removal of waste products, such as smoke and tissue particles, arising during the ablation of biological tissue by means of laser irradiation. According to the invention, discharge openings for a flushing gas are provided, which are arranged such that the gas flows meet above the ablation region at an angle of ca. 100° and stratify to give a gas flow taken up by a suction opening.

8 Claims, 2 Drawing Sheets

U.S. PATENT DOCUMENTS

| | | |
|---|---|---|
| 6,290,695 B1 | 9/2001 | Kuhnert et al. |
| 6,334,683 B2 | 1/2002 | Apple et al. |
| 6,440,109 B1 | 8/2002 | Mastel |
| 6,494,965 B1 * | 12/2002 | Walker et al. ............ 134/21 |
| 6,531,682 B1 * | 3/2003 | Guttler ............ 219/121.84 |
| 6,663,610 B1 | 12/2003 | Thompson et al. |
| 6,752,778 B1 | 6/2004 | Fiedler et al. |
| 6,755,817 B1 * | 6/2004 | Donitzky et al. ............ 606/4 |
| 7,022,941 B2 | 4/2006 | Joseph et al. |
| 7,207,977 B2 * | 4/2007 | Thompson et al. ........ 604/313 |
| 2004/0236392 A1 | 11/2004 | Dick et al. |

* cited by examiner

ARRANGEMENT FOR THE REMOVAL OF WASTE PRODUCTS DURING THE ABLATION OF BIOLOGICAL TISSUE

FIELD OF THE INVENTION

The invention refers to a device for removing residual products, such as smoke and tissue particles, which develop during the ablation of biological tissue by laser radiation.

BACKGROUND OF THE INVENTION

It is well-known that biological tissue can be ablated by applying laser energy without substantial thermal damage of the target areas. This quasi non-thermal process is used for example in medicine for the treatment of cartilage, dental hard tissue, skin areas and also during eye surgery for sculpting the cornea (Photorefractive keratectomy, PRK). Such procedures and the associated device have been published for example in patents DE 197 27 573 C1 and EP 0 412 789 B1. A further procedure, in which the cornea is altered by lasers, is in-situ laser keratomileusis (LASIK). In contrast with PRK, a cut is first made into the cornea and a so-called "flap" is produced, which is folded away during the laser procedure in the work area. After concluding the ablation, which takes place thereby within the cornea, the flap is again folded back.

It is unfavorable that the residual products from the tissue ablation affect the air quality in direct proximity of the treatment place in the form of smoke or tissue particles, which leads to an unpleasant odor for the patient and the treating personnel, and on the other hand that the laser radiation is partially weakened. The latter has a particular relevance in the photorefractive keratectomy, with which the cornea surface is formed by a precise material removal which depends on an unhindered, application of the laser beam, and the fact that the radiation energy is accurately applied with a continuous intensity into the cornea, so that the ablation result can be obtained in the desired quality. The intensity is influenced (reduced) the laser beam produced smoke, vapors and tissue particles, which can lead to irregular and thus unwanted changes in the ablations. In LASIK there also exists the additionally danger that tissue particles may settle on the flap, leading to contamination and degradation of the optical quality.

U.S. Pat. specification No. 5,344,418 describes an implementation in which an applicator is placed close to the outlet of the laser beam with flow channels for gases and/or air, from which during the treatment a gas and/or an air flow may be directed towards the treated tissue, which has as intended consequence that the undesired ablation residual products are blown away from the treatment area.

Hereby the problem of air pollution and unpleasant odor for the patient and operating surgeon is yet not solved.

Also, the technical solution stated in U.S. Pat. specification No. 5,181,916 is not able to eliminate the mentioned disadvantages. Here no gas flow is directed toward the treated area by which the impurities are blown away. Instead the residual gases developing at the treatment place are drawn off with the help of a gas flow. An opening for this purpose is concentrically arranged around the aperture through which the laser beam is directed. This solution has the disadvantage that the visible treated area is only reduced during the treatment since it is partially covered by the opening.

On the applicant's patent DE 100 20 522 A1, the residual products are sucked from the ablation over a channel arranged over the ablation area, and at the same time a withdrawal duct is concentrically arranged around a flushing gas feeding line. This device also covers the treatment area in this case.

This disadvantage also exists in patent DE 101 29 650 A1, in which a circular flow channel is radially and symmetrically arranged around the ablation area, and the gas flow is directed by the discharge openings arranged on the ablation area. Thus the currents meet one another and interact in such a manner that a direction reversal and thus a radially arranged outward current are produced, which carry the ablation products and the developing smoke with them. The problem of the unpleasant odor for the patient and the operating surgeon is not solved in this case.

SUMMARY OF THE INVENTION

Departing from these antecedents, the purpose of the present invention is to avoid the unwanted fluctuations of the laser emission intensity caused by the ablation residual products and to avoid pollution of the environment of the ablation area.

According to the invention, discharge openings are arranged in such a way that the gas flow hits the ablation area symmetrically, and overlap in a resulting gas flow which is directed away from the discharge openings.

In the context of the present invention, at least one opening is intended for the resulting gas flow, which serves for the suction removal of the gas, which carries the residual products.

The smoke coming from the treatment site, developed during the treatment and/or from where the removed tissue particles will be collected by the gas and/or air flow, is directed towards the opening and will be removed from there.

Preferably, the discharge openings expanded as diffusers, so that gas with a smaller flow rate can be directed from these discharge openings and any unwanted gas flow turbulence can be avoided.

In a particularly preferred implementation of the invention, air is the gas and the discharge openings are connected with an air compressor or with a receiver filled with air. Favorable means should be present for the adjustment of the pressure of supplied air as well as with the flow rate at the air compressor and/or at the receiver. These means, such as pressure reducing valves, are sufficiently well-known in the state of the art and do not have to be described here in further detail. Moreover, it is favorable to intentionally humidify the gas flow in order to prevent fast tissue drying at the ablation area.

By superimposing the air flow in the proximity of the ablation area, the gas flow and the tissue particles are quickly moved with the air flow from the location of the laser radiation, so that the laser energy hitting the treatment area is not impaired concerning its intensity or only in a substantially smaller extent than with the state of the art of non transparent particles.

Preferentially it is further intended that the total cross section of the discharge openings and the total cross section of the suction openings are coordinated between one another, so that the positive pressure at the discharge openings and the negative pressure at the suction openings as well as the flow rates in the discharge openings and the flow rates in the suction openings is at a ratio, which lies between 1.1 and 1.3 times the amount of air supplied by the discharge openings.

According to the invention, the unpleasant odor for the patient and the treating physician is avoided and the power density of laser radiation remains as far as possible even by keeping the operation area free vapors and/or tissue particles during the entire duration of the surgery.

In a further aspect of the invention, a mechanism can apply an alternating interruption of the laser radiation hitting the tissue, and the air flow. This way a treatment phase, in which the laser radiation was directed towards the tissue and a partial ablation took place is followed by a suction phase, in which the already described gases and/or air are supplied and/or drawn off and the ablation products are removed. At the end of this "cleaning phase", the gas and/or air flow is interrupted and treatment phase follows again. Here the ablation products are drawn off, there is no odor and the laser radiation path is also kept free of non transparent particles, so that continuous power density radiation can reach the tissue.

In another aspect of the invention infrared light sources for lighting the environment of the ablation area are arranged in the proximity of the discharge openings and/or the suction openings. With these light sources, the iris can be illuminated with the purpose of tracking the pupil movement, as it is described for example in U.S. Pat. No. 6,334,683, whose entire contents are hereby incorporated by reference. This results in particularly compact units, which achieve both removal of the residual products and make additional light sources for the eye tracker devices redundant. Thus the structure of such treatment equipment is simplified by having fewer disturbing elements in the vision field of the operating surgeon.

BRIEF DESCRIPTION OF THE DRAWINGS

The invention will be described in more detail below based on an example. On FIG. 1, the associated drawings show a basic representation of the invention in a plan view, and a perspective view on FIG. 2.

DETAILED DESCRIPTION

Figure 1:
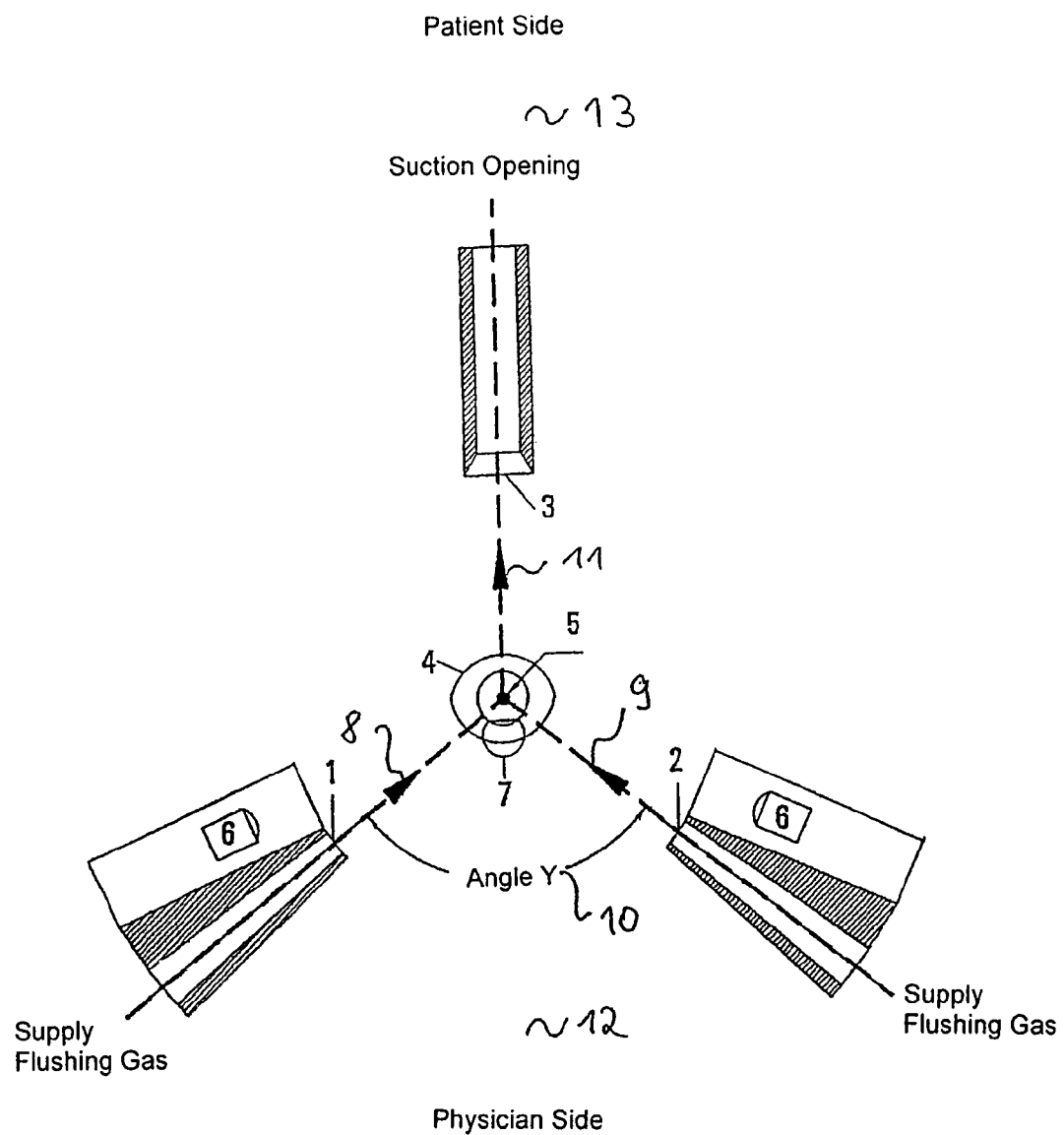

FIG. 1 shows two discharge openings 1 & 2, through which the flushing gas is directed to the ablation area, as well as a suction opening 3, by which the flushing gas is extracted along with the ablation particles bound therein. The ablation area 5 of the cornea of an eye 4 is hereby represented, in which a flap 7 was cut and folded back.

The stream axes 8 & 9 of the flushing gas supply cross here the Z-axis of the treatment laser (not shown) in the working plane of the laser treatment. This Z-axis stands perpendicularly on the reference level of FIG. 1. Both gas flows 8, 9 overlay when they meet each other and form a united current along axis 11, which is directed towards suction opening 3.

Thus results a Y-shaped arrangement of the gas openings separated from each other, whereby a Y is arranged towards direction 13 of the patient's feet and the open side 12 is turned towards the operating surgeon. In an example arrangement, a gas flow (0.5-10 m/s) is directed from discharge openings 1 and 2 towards eye 4. These two gas flows have the same flow rates. The discharge openings are arranged such that the gas flows in ablation area 5 meet and are united in a resulting current towards suction opening 3. The resulting current is then extracted by suction opening 3.

When both air flows unite in the ablation area, they cause a particularly intensive gas throughput that effectively removes particulates from the ablation area. Deposits of particles on flap 7 are prevented by the air flow direction and the intensive gas throughput. The particles that cause the unpleasant odor for both the physician and the patient are minimized this way.

In one embodiment the described effect is achieved if the discharge openings have a diameter of 6 mm and the gas flow passes the ablation area with a speed of 3 m/s. The negative suction pressure is coordinated in such a way that the resulting gas flow at the suction nozzle is taken up, for example with a flow rate of 3 L/S.

The incidence angle of the gas flows in relation with the horizontal plane is approximately within the range of 40°±15°, and the Y-angle 10 is around 100°±20°. The size of the angles and the arrangements of the elements ensure that the gas flows will be obstructed as little as possible by the anatomy of the head (nose, brows, etc.).

The distance between discharge openings 1, 2 and/or suction opening 3 and the ablation area 5 is about 75 mm±10 mm. These distances leave the treating physician with a movement clearance with an almost unhindered access to ablation area 5.

The lighting sources 6 for ablation area 5 are structurally united with discharge openings 1, 2 and suction opening 3, and may be infrared light sources which serve as light sources for a camera (not represented here), whose pictures can be evaluated for the tracking the pupil location and thus the line of sight of the patient. Procedures for this evaluation are well-known by the specialists, and are not described in more detail here. As a reference, please consult U.S. Pat. No. 6,334,683.

The third infrared radiation source 6, not represented in FIG. 1, may be located above suction opening 3.

The IR radiation sources are arranged at an angle of about 120° to each other, whereby the infrared radiation necessary for eye tracking is not obstructed by the patient's head anatomy and thus the evaluation use of the pictures taken by the camera is significantly improved.

By arranging the discharge openings on the physician side, on one hand it is made possible to achieve the currently favorable Y-angles of 100°, and on the other hand allow the optimal angles of 120° required for the IR irradiation mechanisms.

This arrangement of the IR radiation sources and the discharge and/or suction openings provide easy accessibility to ablation area 5 with improved ergonomics for the operating surgeon and additionally improve the functional lighting requirements for the eye tracking device as well as reduces the presence of residual products in the ablation area.

The extraction and suction units can be easily fastened with corresponding guides (which are not represented here), and which can be removed for cleaning or sterilizing without significant efforts.

In a further implementation, the gas flows will provide constant temperature and air humidity. That also includes the intentional humidification of the gas flows with ultrasonic fog, in order to achieve even more constant conditions in the ablation area.

Figure 2:
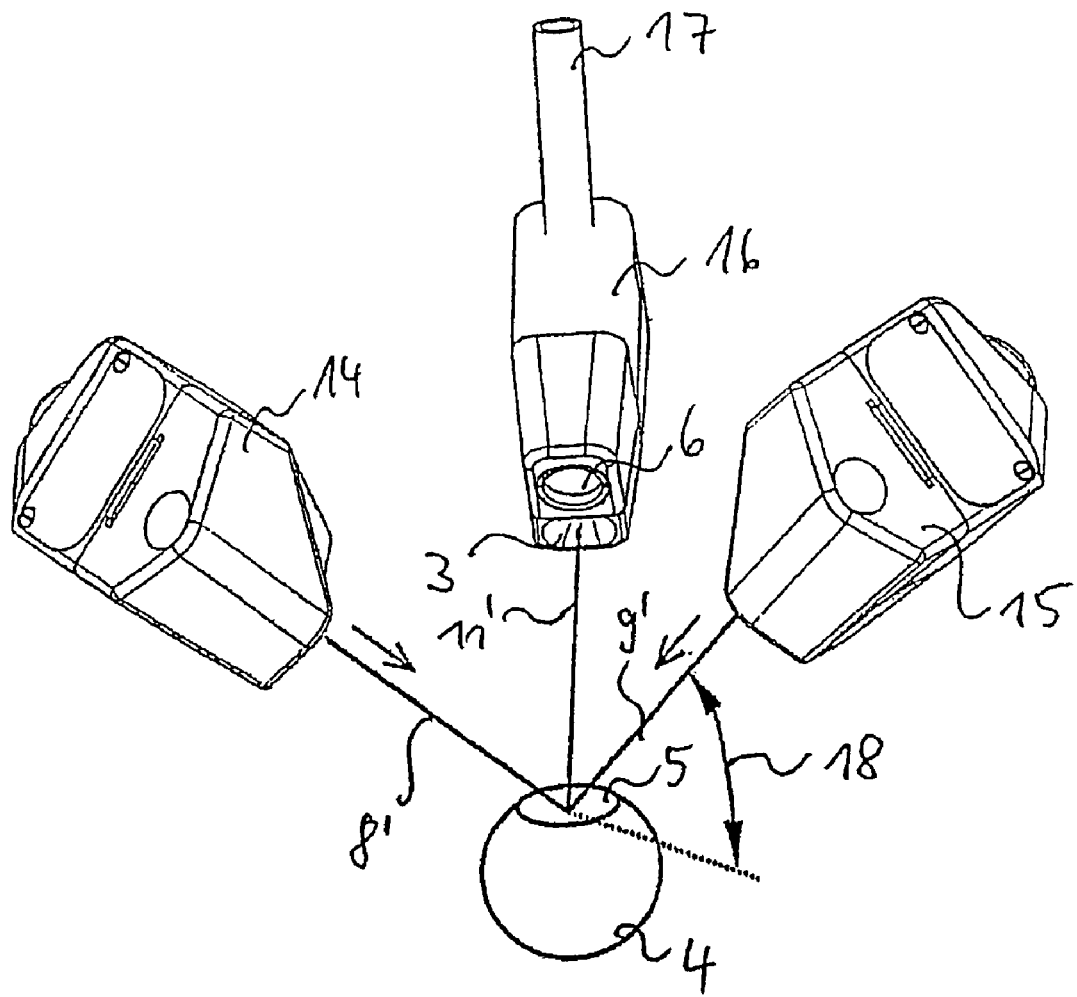

FIG. 2 shows the implementation shown in FIG. 1 in a perspective view. Both units 14 and 15 are depicted from the rear and therefore discharge openings 1 and 2 and IR lighting source 6, which are directed towards the ablation area 5 of eye 4, are not visible. Unit 16 also includes suction opening 3, and an IR lighting source 6 is connected to an extraction duct 17. Angles 18 of axes 8', 9' and 11' from working plane 5 amount to 40°±15°.

Discharge openings 1, 2 and suction opening 3 are connected with conduits, which for example are connected with a compressor or a pressurized air reservoir (for openings 1, 2) and/or to a suction device (for opening 3).

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. A method of removing residual products from the ablation of biological tissue of a patient's eye by laser radiation and avoiding an odor nuisance to the patient, comprising:
   directing at least two flows of flushing gas such that the at least two flows meet at an ablation area on the eye and substantially unite to form a resulting gas flow, the two flows and the resulting gas flow forming a Y-shape;
   directing the gas flows towards the ablation area on the eye at a mutual angle of one hundred degrees plus or minus twenty degrees; and
   extracting the resulting gas flow from the ablation area on the eye.

2. A method of removing residual products as claimed in claim 1, further comprising arranging an extraction opening such that the resulting gas flow is directed toward the extraction opening.

3. A method of removing residual products as claimed in claim 1, further comprising arranging the extraction opening at an angle of one hundred thirty degrees plus or minus ten degrees to the discharge openings.

4. A method of removing residual products as claimed in claim 1, further comprising arranging the gas flows such that the gas flows form an angle of forty degrees plus or minus fifteen degrees relative to an ablation plane proximate the ablation area.

5. A method of removing residual products as claimed in claim 1, further comprising directing at least one lighting source generally toward the ablation area.

6. A method of removing residual products as claimed in claim 5, further comprising operably connecting the at least one lighting source such that the lighting source is directed generally parallel to one of the flows of flushing gas or the resulting gas flow.

7. A method of removing residual products as claimed in claim 6, further comprising directing three lighting sources and orienting the lighting sources such that they are arranged at a mutual angle of one hundred twenty degrees.

8. A method of removing residual products as claimed in claim 1, further comprising extracting the resulting gas flow through a suction opening such that a distance between the suction opening and the ablation area is seventy five millimeters plus or minus ten millimeters and discharging the at least two flows of flushing gas from at least two discharge openings, respectively, wherein a distance between the discharge openings and the ablation area is seventy five millimeters plus or minus ten millimeters.

* * * * *